United States Patent [19]
Spaeth et al.

[11] Patent Number: 5,312,416
[45] Date of Patent: May 17, 1994

[54] METHOD AND SYSTEM FOR ENCLOSING, MANIPULATING, DEBULKING AND REMOVING TISSUE THROUGH MINIMAL ACCESS INCISIONS

[75] Inventors: Edmund E. Spaeth, Orange; Alexander S. Borsanyi, Newport Beach; Thomas L. Hursman, Diamond Bar, all of Calif.

[73] Assignee: Endomedix Corporation, Irvine, Calif.

[21] Appl. No.: 779,443

[22] Filed: Oct. 18, 1991

[51] Int. Cl.⁵ .............................................. A61B 17/00
[52] U.S. Cl. ...................................... 606/114; 128/749; 606/110; 606/113; 606/127
[58] Field of Search ................... 600/37; 128/849–851; 604/23, 26, 27, 171, 172, 264, 318; 606/1, 108, 110, 113, 114, 127, 128

[56] References Cited

U.S. PATENT DOCUMENTS

| | | |
|---|---|---|
| 15,477 | 3/1874 | Bradford . |
| 30,471 | 10/1960 | Dudley .................................. 606/127 |
| 1,609,014 | 9/1925 | Dowd . |
| 3,472,230 | 10/1969 | Fogarty ............................... 606/127 |
| 3,828,790 | 8/1974 | Curtiss et al. ...................... 606/113 |
| 3,908,661 | 9/1975 | Kramer ................................ 606/127 |
| 4,557,255 | 12/1985 | Goodman . |
| 4,790,812 | 12/1988 | Hawkins et al. ...................... 604/27 |
| 4,997,435 | 3/1991 | Demeeter ............................. 606/127 |
| 5,037,379 | 8/1991 | Clayman et al. ...................... 604/27 |
| 5,074,867 | 12/1991 | Wilk ................................... 606/127 |
| 5,143,082 | 9/1992 | Kindberg et al. ................... 128/749 |
| 5,147,371 | 9/1992 | Washington ........................ 606/113 |
| 5,171,314 | 12/1992 | Dulebohn ............................ 606/113 |
| 5,176,687 | 1/1993 | Hasson et al. ...................... 606/127 |
| 5,190,542 | 3/1993 | Nakao et al. ....................... 606/113 |
| 5,190,555 | 3/1993 | Wetter et al. ....................... 606/113 |
| 5,192,284 | 3/1993 | Pleatman ............................. 606/127 |
| 5,192,286 | 3/1993 | Phan et al. ......................... 1006/113 |
| 5,201,740 | 4/1993 | Nakao et al. ....................... 606/113 |

FOREIGN PATENT DOCUMENTS

| | | | |
|---|---|---|---|
| 0025796 | 1/1884 | Brazil | .................................. 606/127 |
| 3522649 | 1/1986 | Fed. Rep. of Germany | ...... 606/127 |

OTHER PUBLICATIONS

Complete Evisceration of Small Bowel During Operation on Colon Davol Rubber Co. Catalogue p. 24 1959.

*Primary Examiner*—Stephen C. Pellegrino
*Assistant Examiner*—Glenn Dawson
*Attorney, Agent, or Firm*—Stetina and Brunda

[57] ABSTRACT

The present invention pertains to a device for deploying and retrieving a flexible tissue containment sac within a body cavity, through a minimal access incision. The device generally includes a tubular introducer having a flexible tissue containment sac disposable in a compressed configuration within the lumen of such tubular introducer. An elongate plunger shaft or pushing member is insertable or passable through at least a portion of the introducer lumen to push the containment sac out of the distal end of the lumen. Attached to the containment sac and extending through the lumen of the introducer is a tether. A portion of the tether may extend out of the proximal end of the introducer. The proximal end of the tether may be grasped and pulled in a proximal direction to pull the containment sac to a retrieved position on the end of an extractable shaft or, in embodiments absent such extractable shaft, to pull at least a portion of the containment sac into the introducer lumen.

41 Claims, 8 Drawing Sheets

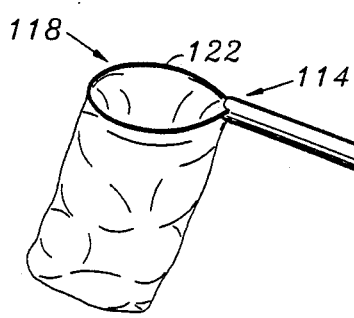
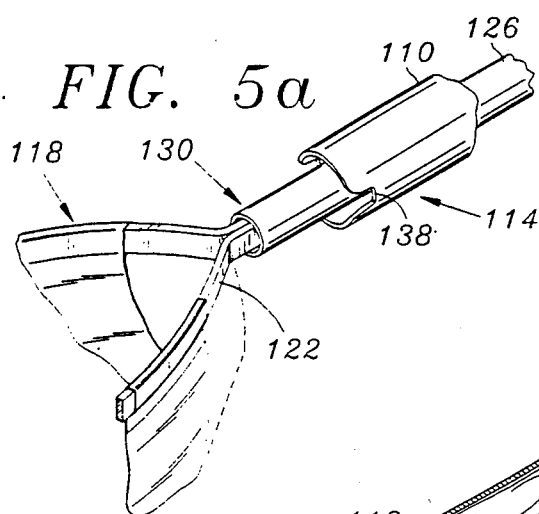
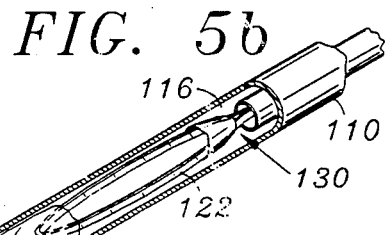
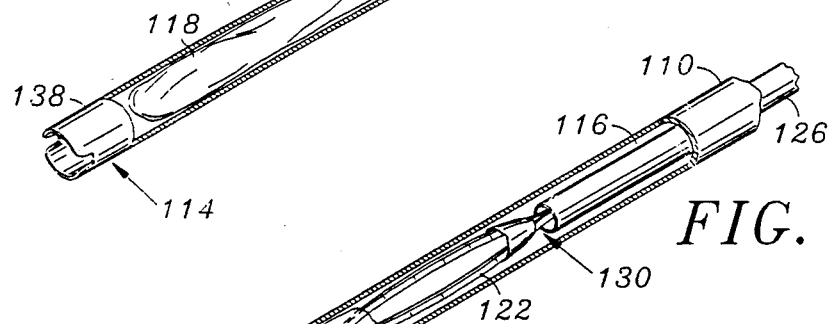
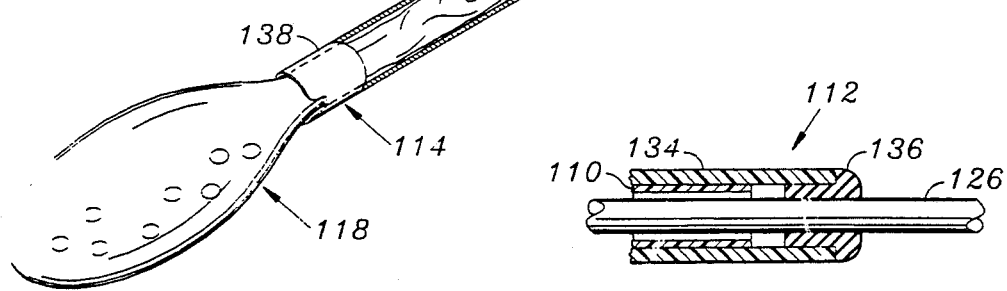

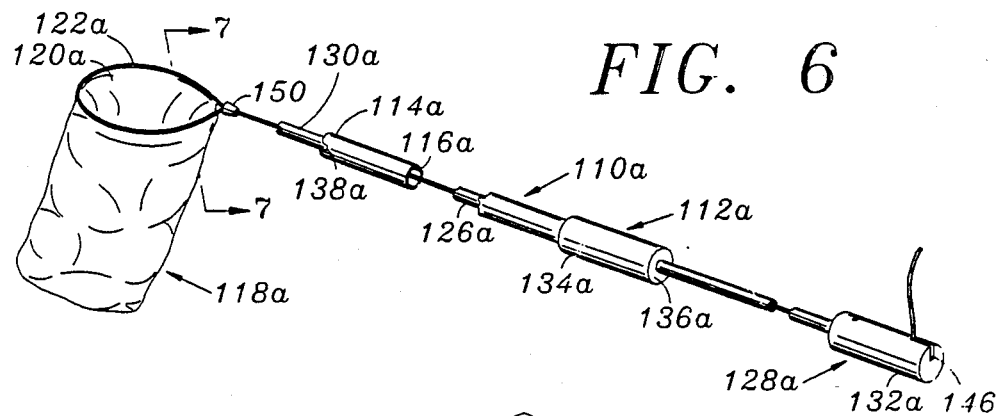
FIG. 6
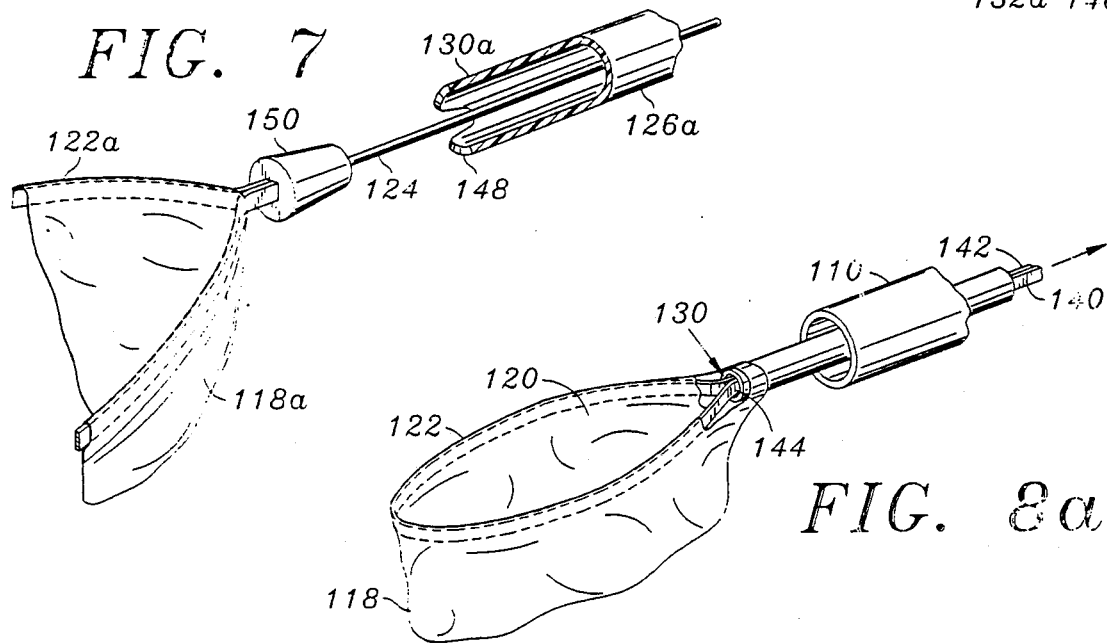
FIG. 7
FIG. 8a
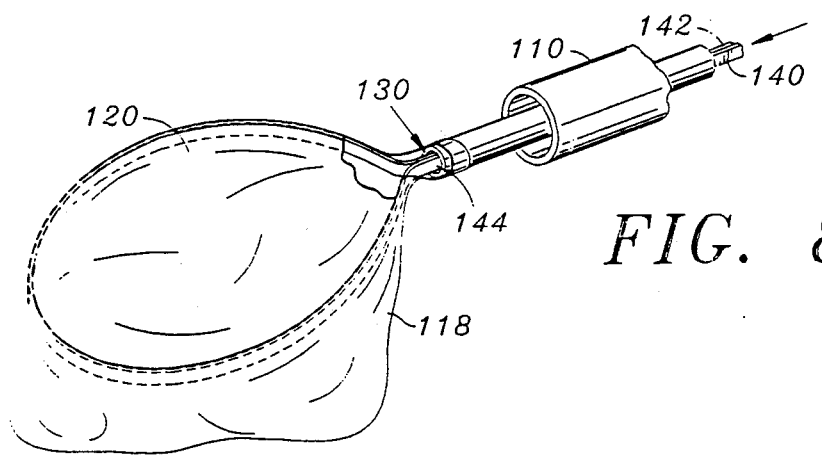
FIG. 8b

5,312,416

METHOD AND SYSTEM FOR ENCLOSING, MANIPULATING, DEBULKING AND REMOVING TISSUE THROUGH MINIMAL ACCESS INCISIONS

FIELD OF THE INVENTION

This invention relates generally to medical equipment and, more particularly to a method and system for percutaneously inserting a flexible containment sac or bag into a body cavity for containment of excised tissue or matter and subsequent removal of such tissue or matter from the body cavity.

BACKGROUND OF THE INVENTION

The advent of modern endoscopic surgical procedures (e.g. laparoscopic procedures) has enabled the performance of complex excisional surgery through minimal access incisions of approximately 1 centimeter or less. Such excisional procedures may be utilized to excise or resect relatively large volumes of tissue, tumors, organs and the like. The extraction and removal of such excised tissues, tumors, organism or the like is, however, sometimes problematic because such excised tissue, tumors, organs or the like are often too large or too bulky to be removed directly through the minimal access (e.g. 1 cm) endoscopic incision. Also, the excision, manipulation and removal of certain non-benign matter (e.g. infected tissue, fecally contaminated segments of bowel, cancerous tumors) is complicated by the need to contain such non-benign matter in a manner that will prevent or deter dissemination or spread of such non-benign matter within the body cavity.

Accordingly, there exists a need in the art for new appliances and apparatus for containing, manipulating, liquidizing or debulking, and/or removing excised tissues, tumors, organs or other matter, through relatively small minimal access incisions.

A surgical tissue bag and method for percutaneously debulking tissue is purportedly described in U. S. Pat. No. 5,037,379 (Clayman et al.).

A surgical tissue sac for use in endoscopic surgical procedures is presently available commercially under the name ENDOPOUCH ™ (Ethicon, Inc., Division of Johnson & Johnson, Route 22, P. O. Box 151, Somerville, New Jersey 08876).

The surgical tissue containment sacs of the prior art may present certain shortcomings in that such prior devices (a) do not adequately open or fully expand when inserted into a body cavity through a minimal access incision, (b) lack means for maintaining directional orientation of the bag opening during intracorporeal usage, (c) lack sufficient transparency to permit ease of viewing through the wall of the containment sac and/or (d) lack means for facilitating passage of instruments into the containment sac for purposes of treating, grinding, debulking or removing material from the interior of the sac.

SUMMARY OF THE INVENTION

The present invention overcomes some or all of the shortcomings of the prior art by providing a method and system for introducing a flexible containment sac into a body cavity and for subsequently exteriorizing at least a portion of the containment sac so as to permit a debulking, grinding or liquidization apparatus to be inserted thereinto for the purpose of processing and removing the contents of the containment sac. Thereafter, the emptied or partially emptied containment sac may be fully extracted from the body cavity through the existing minimal access (e.g. 1 cm) incision.

In accordance with the invention, there is provided a first embodiment of a system for deploying and retrieving a flexible tissue containment sac within a body cavity, said system comprising a tubular introducer and a flexible tissue containment sac having at least one aperture or opening formed therein. The containment sac is disposable in a "compressed" state whereby it may be initially packed or inserted into the lumen of the tubular introducer. An elongate plunger is subsequently insertable through at least a portion of the lumen of the introducer to expel said containment sac out of the distal end of said lumen. A tether member or attachment cord is attached to the containment sac and extends through the lumen of the introducer such that, after the containment sac has been deployed out of the distal end of the introducer, the tether may be utilized to subsequently pull or withdraw at least a portion of the containment sac back into the distal end of the introducer sheath.

Further in accordance with the invention, there is provided a second embodiment of a system for deploying and retrieving a flexible tissue containment sac within a body cavity Such second embodiment comprises (a) a tubular introducer; (b) a rigid shaft member extendable through said tubular introducer; and (c) a flexible containment sac positioned on the distal end of said rigid shaft member. The rigid shaft member is movable within the lumen of said introducer between a "first" position wherein the containment sac is withdrawn into the lumen of said introducer and a "second" distally advanced position wherein the containment sac is deployed beyond the distal end of said introducer.

Further in accordance with either embodiment of the invention, the flexible containment sac may incorporate one or more opening apparatus or biasing means such as resilient strips, inflatable members, springs or movable members for urging the deployed containment sac to an open configuration such that matter may easily be passed into and through the aperture or opening of the sac or into the interior of the sac. For example, a resilient or biased rim member may be disposed about the aperture or opening of the containment sac such that, when withdrawn into the lumen of the introducer, the rim member will be compressed into a collapsed or closed configuration but when disposed out of the distal end of the introducer the rim member will resiliently or otherwise expand from such compressed configuration to an open configuration. Such resilient or biased rim member may be formed of plastic strip, spring metal wire, metal or metal alloys which exhibit superelastic properties such as certain shape memory alloys (e.g. nickel-titanium alloys), or any other suitable material having sufficient memory to achieve the desired opening function. Alternatively, the rim member may be formed of first and second rim member portions attached by way of a spring or biased hinge adapted to urge said first and second rim member portions in divergent directions, thereby biasing the flexible containment sac to an open configuration. In addition, the sac may be inflatable in other areas. For example, the sac may be formed of separate inner and outer layers (e.g. a bag within a bag) such that an inflatable space or cavity exists between the inner and outer layers. A means for passing inflation fluid and/or gas into such inflation space(s), such as a hollow inflation lumen extending through the tether, may be fluidly connected to the inflation space(s) and usable for the purpose of inflating and deflating the sac. Inflation of the sac will result in full opening and expansion of the sac while deflation thereof will permit the sac to assume a collapsed, non-expanded configuration. When inflated, the inner sac layer may be sufficiently separated from the outer sac layer such that, if the inner sac layer is punctured, the outer sac layer will remain intact, thereby serving to deter or prevent untoward leakage of matter from the interior of the sac. Also, an inflatable rim member may be utilized such that, upon inflation of the rim member, the opening of the sac will expand to an open configuration.

Still further in accordance with either embodiment of the invention, the distal end of the tubular introducer may include a notch configured to receive therein the rim member of the containment sac such that when the tether is partially withdrawn in a proximal direction, the rim member will seat within the notch such that rotation or other movement of the sac will be thereby deterred or prevented.

Still further in accordance with either embodiment of the invention, a quantity of lubricant and/or a surface modified layer such as a layer of lubricant may be disposed on the outer surface of the flexible containment sac to facilitate passage of the sac into and out of the tubular introducer and to provide additional or enhanced tissue compatibility.

Still further in accordance with the invention, the size and/or shape of the flexible containment sac may be varied to optimize its use in various applications. Applications of the invention may include removal of organs such as the gallbladder or appendix, removal of tumors, removal of excised or resected masses of tissue, or removal of calculi from an in situ organ such as the gallbladder. Still further in accordance with the invention, the thickness or strength of the containment sac may be altered depending on the desired application. In applications where rigid debulking or liquidizing instruments, forceps, etc. are to be inserted into the containment sac it is desirable that the containment sac be formed of relatively puncture resistant material(s) such as 1.5 mil. polyethylene sheet. The construction of the containment sac is, however, not limited to a single layer 1.5 mil. polyethylene sheet and, in fact, various other materials may also be used, as well as reinforcements (double thickness film, mesh laminate, etc.) at critical stress points.

Still further in accordance with the invention, the containment sac may be formed of single walled pliable material such as single walled plastic sheet.

Still further in accordance with the invention, the flexible containment sac may be formed of transparent material so as to permit endoscopic visualization of the contents of the sac during the operative procedure.

Further objects and advantages of the invention will become apparent to those skilled in the art upon reading and understanding of the following detailed description and the accompanying drawings.

BRIEF DESCRIPTION OF THE DRAWINGS

FIG. 5 is a perspective view of a second embodiment of the present invention;

FIG. 5a is an enlarged perspective view of the distal end of the device shown in FIG. 5;

FIG. 5b is a longitudinal sectional view through line 5b—5b of FIG. 5;

FIG. 5c is a cut-away perspective view of a portion of the device shown in FIG. 5 illustrating partial withdrawal of the containment sac into the introducer sheath with the filled portion of the containment sac remaining beyond the distal end of the introducer sheath;

FIG. 5d is a cut-away perspective view of a portion of the device shown in FIG. 5 illustrating complete withdrawal of the containment sac into the lumen of the introducer sheath;

FIG. 6 is a modified version of the second embodiment of the present invention incorporating a detachable containment sac and a containment sac tether extending therethrough;

FIG. 7 is a cut-away perspective view of the distal end of the device shown in FIG. 6;

FIG. 8a is a perspective view of the distal end of a device in accordance with the second embodiment of the invention incorporating a slidable sac opening apparatus in a "collapsed" disposition;

FIG. 8b is a perspective view of the distal end of a device in accordance with the second embodiment of the invention incorporating a slidable sac opening apparatus in a "open" disposition;

FIG. 9b is an enlarged view of a portion of the sac rim of FIG. 9a;

DETAILED DESCRIPTION OF THE PREFERRED EMBODIMENT

Figure 1:
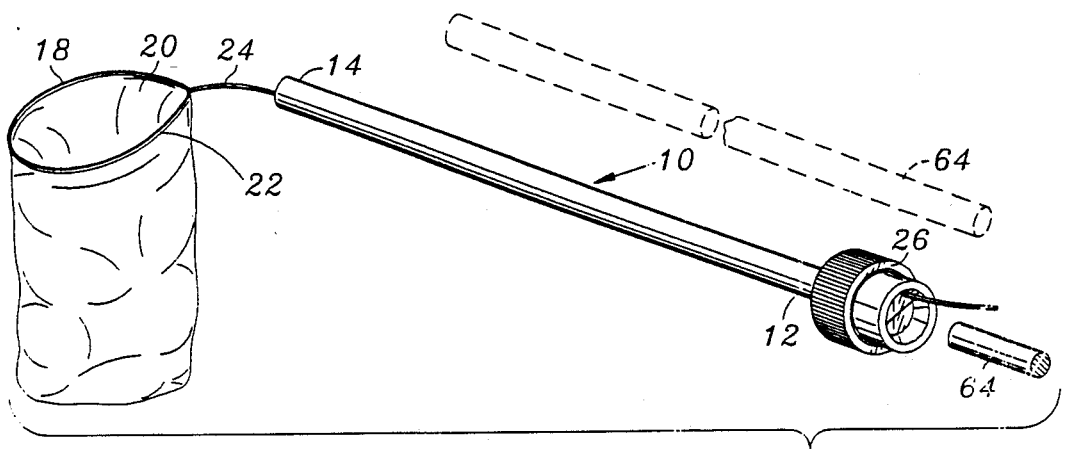
FIG. 1 is a perspective view of a first embodiment of the present invention.
Figure 2:
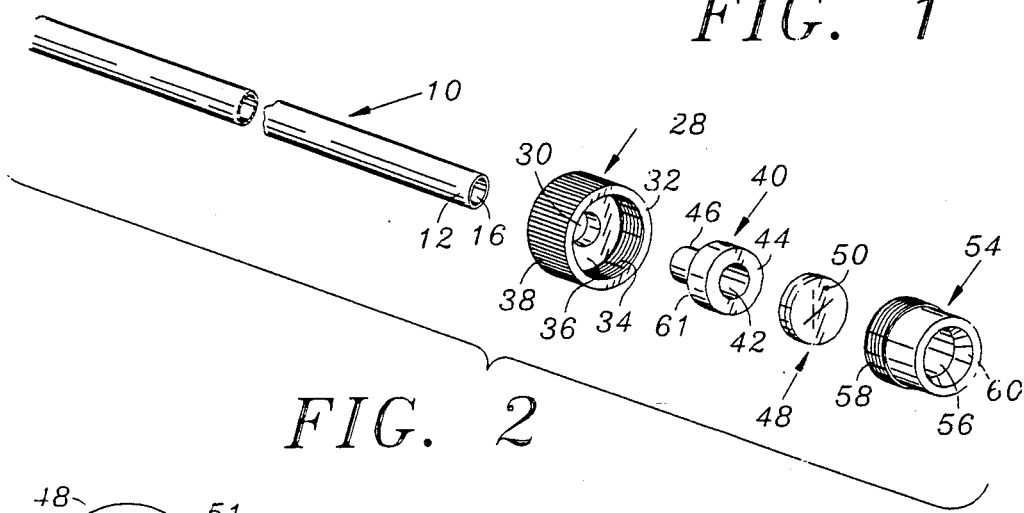
FIG. 2 is an exploded view of the introducer portion of a first embodiment of the present invention.
Figure 2B:
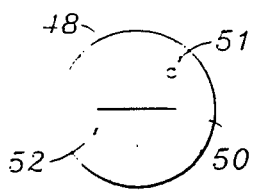
FIG. 2b is a plan view of a preferred seal member used in connection with the introducer sheath of the first embodiment of the present invention.
Figure 2C:
FIG. 2c is an exploded view of the seal member shown in FIG. 2b.
Figure 2A:
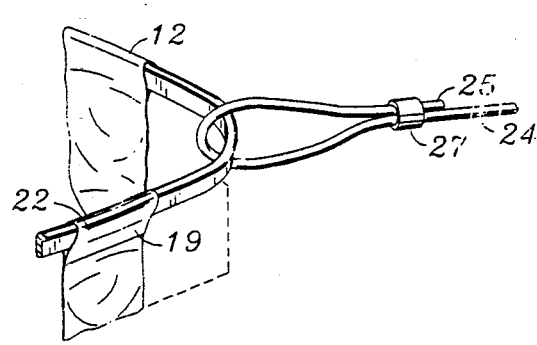
FIG. 2a is a cut-away view of a portion of a flexible containment sac which is incorporated in the first embodiment of the present invention.

Referring now to the drawings wherein the showings are for purposes of illustrating preferred embodiments of the present invention only, and not for purposes of limiting the same, FIGS. 1-2c illustrate a system for deploying and retrieving a flexible tissue containment sac within a body cavity constructed in accordance with a first embodiment of the present invention. In the first embodiment, the deployment and retrieval system generally comprises an elongate tubular introducer or sheath 10 having a proximal end 12, a distal end 14 and a hollow lumen 16 extending longitudinally therethrough. Interfaced to the introducer 10 is a flexible tissue containment sac 18 having at least one aperture 20 formed therein to provide access to the interior of the sac 18, and a rim member 22 disposed about the periphery of the aperture 20. Rigidly attached to sac 18, and more particularly to rim member 22, is a tether 24 which is extendable through the lumen 16 of the introducer 10 as will be described in greater detail below. As best seen in FIG. 2a, in fabricating the sac 18 the rim member 22 is preferably attached thereto via a heat fusion process. In this respect, the upper edge 19 of the sac 18 is folded over the rim member 22 and fused to the sac 18. It will be recognized that other attachment methods, such as the use of adhesives, may be utilized as an alternative to the heat fusion attachment process. Additionally, as an alternative to being rigidly attached to the rim member 22, the tether 24 may be attached to the rim member 22 such that the rim member 22 may swivel relative to the tether 24. Particularly, the distal end 25 of the tether 24 is wrapped about the rim member 22 and attached to the tether 24 via a fastener such as a clip 27.

In the first embodiment, the containment sac 18 is alternately disposable between a "deployed" state as shown in FIG. 1 and a "compressed" state whereby the sac 18 is pulled into and disposed within the lumen 16 of the introducer 10. As will be recognized, when the introducer 10 is initially inserted into the abdominal cavity of a human being, the sac 18 will be disposed in the compressed state within the introducer 10. After insertion into the abdominal cavity occurs, the sac 18 will be disposed to the deployed state to allow large tissues, tumors or organs to be placed thereinto. Advantageously, the rim member 22 is biased to force the aperture 20 to an open configuration when the sac 18 is moved from the compressed state to the deployed state. Importantly, by heat fusing the sac 18 to the rim member 22, the potential for the sac 18 to be torn when moving from the compressed state to the deployed state is substantially reduced. In the first embodiment, the rim member 22 comprises a plastic strip possessing sufficient resiliency to force the aperture 20 open when the sac 18 is deployed. However, alternative methods and materials may be used in constructing rim member 22 to facilitate such opening, as will be discussed in greater detail below.

Referring now to FIGS. 1 and 2, the proximal end 12 of introducer 10 includes a seal assembly 26 which is adapted to provide a gripping surface for the introducer 10 and substantially prevent fluid flow through the lumen 16 when the introducer 10 is inserted into the abdominal cavity. As best seen in FIG. 2, seal assembly 26 generally comprises a grip member 28 having a generally cylindrical configuration and including a bore 30 extending axially therethrough which is sized to receive the proximal end 12 of the introducer 10. Grip member 28 further includes an annular flange portion 32 having a female thread 34 formed on the inner surface thereof which terminates at an annular inner wall 36. Additionally, formed on the exterior surface of the grip member 28 are a plurality of serration 38 which aid in preventing slippage of the user's hand therefrom. Rigidly secured to the proximal end 12 of the introducer 10 is a flange member 40 having a bore 42 extending axially therethrough and an annular planar surface 44 extending about the bore 42. Flange member 44 is formed to include a tapered portion 46 and thus defines two different outer diameter dimensions. Importantly, the tapered portion 46 of flange member 40 is secured to the proximal end 12 such that the bore 42 extending therethrough is in substantial coaxial alignment with the lumen 16 extending through the introducer 10.

Disposed upon the annular planar surface 44 of flange member 40 is a seal member 48. In the first embodiment, seal member 48 is constructed so as to have an outer diameter dimension equal to the largest outer diameter dimension of the flange member 40. As such, seal member 48 is sized to completely cover the bore 42 of flange member 40 when placed upon annular surface 44. As will be recognized, due to the sizing of the seal member 48, the seal member 48 is operable to substantially prevent fluid flow through the lumen 16. As seen in FIGS. 2b and 2c, seal member 48 preferably comprises a first member 49 and a second member 51 which are preferably secured to one another via an adhesive. Disposed within the seal member 48 is a first aperture 50 which extends axially therethrough, i.e. through first member 49 and second member 51, and is sized and configured to receive tether 24 in a manner establishing a fluid tight closure around the tether 24 while permitting the tether 24 to move back and forth therethrough. The seal member 48 further includes a second aperture 52 formed by a first slit 53 in first member 49 and a second slit 55 in second member 51 which intersect one another at a 90-degree angle when first member 49 is attached to second member 51, thus biasing the second aperture 52 to a closed configuration. The second aperture 52 is utilized for reasons which will be discussed in greater detail below. The seal member 48 is preferably constructed from an elastomeric material. Additionally, it will be recognized that other seal designs and configurations may be used as an alternative to seal member 48.

The final component comprising the seal assembly 26 is a retainer member 54 having a generally cylindrical configuration and including a bore 56 extending axially therethrough. Formed upon a portion of the outer surface of retainer member 54 adjacent one end thereof is a male thread 58 which is sized and configured to be threadably receivable into the female thread 34 of grip member 28. Additionally, retainer member 54 includes a chamfered portion 60 formed about the periphery of the bore 56 adjacent the end of retainer member 54 opposite that upon which the male thread 58 is formed. Though not shown in FIG. 2, an annular inner surface is defined within the bore 56 of retainer member 54.

Seal assembly 26 is interfaced to the proximal end 12 of introducer 10 by first securing the tapered portion 46 of the flange member 40 thereto via an adhesive. Grip member 28 is then placed over the distal end 14 of the introducer 10 and slid along the length thereof until the inner wall 36 formed therein is directly abutted against a step 61 defined by the tapered portion 46 of the flange member 40. The seal member 48 is then placed upon the annular planar surface 44 of the flange member 40. The seal member 48 is maintained in this particular orientation by the engagement of the retainer member 54 to the grip member 28 via the threadable receipt of the male thread 58 into the female thread 34. In this respect, when such threadable engagement occurs the seal member 48 is compressed between the annular planar surface 44 of the flange member 40 and the annular inner surface defined within the bore 56 of the retainer member 54.

As previously specified, the sac 18 is disposable between a compressed state wherein the sac is disposed within the lumen 16 and a deployed state wherein the sac 18 is extended into the abdominal cavity. To facilitate the movement of the sac 18 from the compressed state to the deployed state, there is provided an elongate plunger 64 as seen in FIG. 1. Plunger 64 is sized and configured to be insertable through at least a portion of the lumen 16 of the introducer 10 to expel the containment sac 18 from the distal end 14 thereof. The plunger 64 is preferably configured to include a longitudinally extending groove or aperture therein to allow the tether 24 to pass therethrough in an unobstructed manner. As also previously indicated, the seal assembly 26, and more particularly the seal member 48, is configured to substantially prevent fluid flow through the lumen 16. In this respect, the second aperture 52 is sized and configured to allow the plunger 64 to be inserted therethrough to deploy the sac 18 while maintaining a fluid-tight seal thereabout. When the plunger 64 is not inserted therethrough, the second aperture 52 is biased to the "closed" configuration thereby preventing fluid flow through the lumen 16. Advantageously, the chamfered portion 60 of retainer member 54 facilitates the easy entry of plunger 64 into the introducer 10.

As best seen in FIG. 1, in interfacing the containment sac 18 to the introducer 10, the tether 24 is extended through the hollow lumen 16 and seal assembly 26. As will be recognized, when the sac 18 is initially deployed from the distal end 14 of the introducer 10, the tether 24 is pulled through the lumen 16 and seal member 48 toward the distal end 14 of the introducer 10. As will be discussed in greater detail below, after large tissues, tumors or organs have been placed into the sac 18, the sac 18 is at least partially retracted into the distal end 14 of the introducer 10. Such partial retraction is facilitated by the pulling of the tether 24 through the lumen 16 and seal member 48 in a direction toward the proximal end 12 of the introducer 10. Since the seal member 48 is used to prevent fluid flow through the lumen 16, the first aperture 50 is sized to establish a fluid-tight closure around the tether 24 while allowing the tether 24 to move back and forth therethrough. The tether 24 is preferably formed of a monofilament nylon line, though other materials such as a rigid plastic strip material may be utilized as an alternative. Importantly, the tether 24 is sized so as to protrude from the proximal end 12 of the introducer 10 when the sac 18 is deployed from the distal end 14 thereof, thereby enabling at least a portion of the sac 18 to be redrawn into the lumen 16 of the introducer 10 when the protruding portion of the tether 24 is grasped and pulled in the proximal direction.

Figure 3:
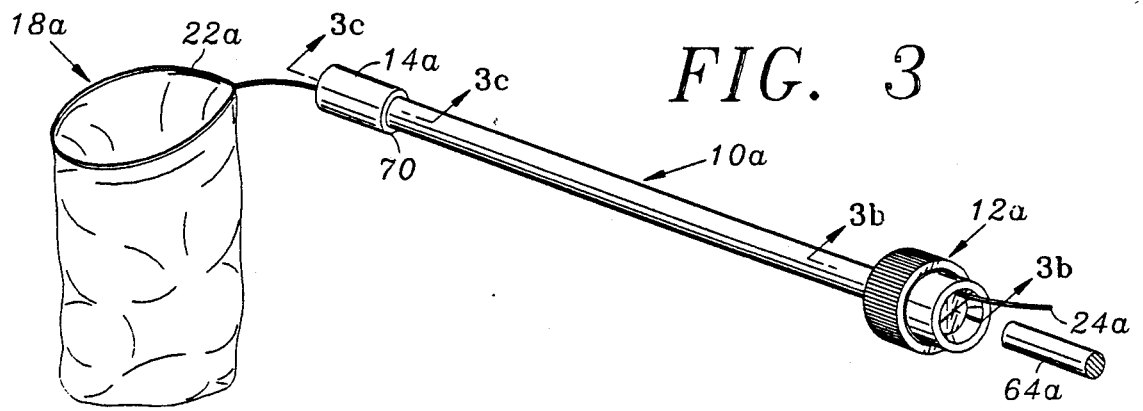
FIG. 3 is a perspective view of a modified version of the first embodiment of the present invention incorporating an optional containment sac withdrawal guide member on the distal end of the introducer sheath.
Figure 3A:
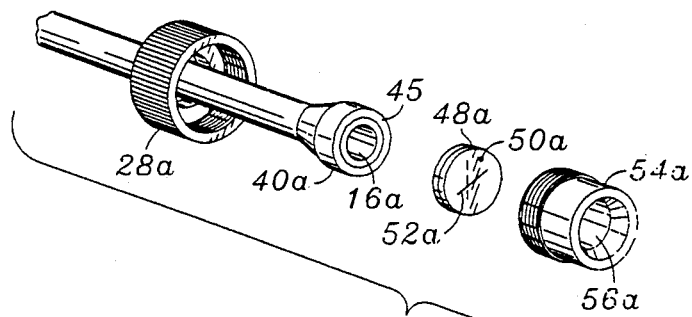
FIG. 3a is an exploded view of the proximal end assembly of the introducer sheath portion of the modified version of the first embodiment of the present invention.
Figure 3C:
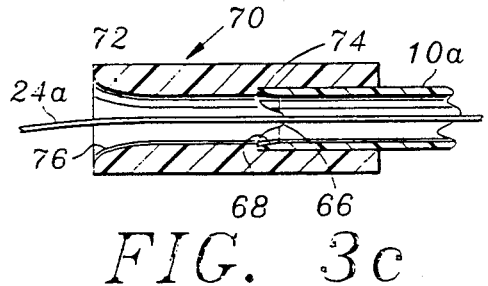
FIG. 3c is a longitudinal sectional view through line 3c—3c of FIG. 3.
Figure 3B:
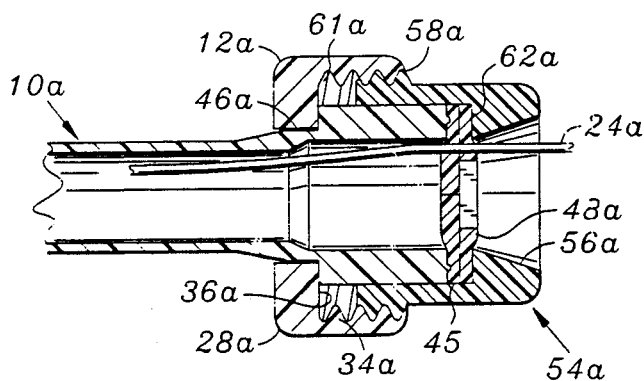
FIG. 3b is a longitudinal sectional view through line 3b—3b of FIG. 3.
Figure 3D:
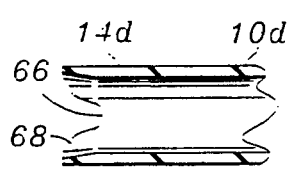
FIG. 3d is a longitudinal sectional view of the distal tip of the introducer portion of the device shown in FIG. 3 without the optional sac withdrawal guide member positioned thereon.
Figure 4:
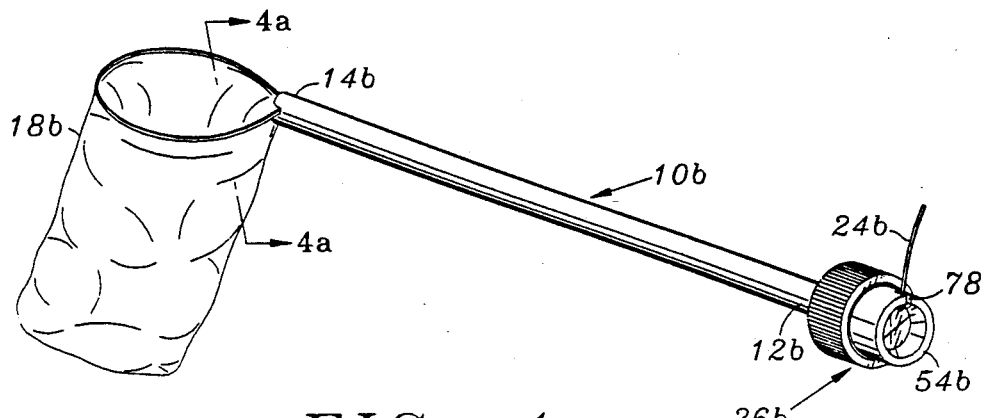
FIG. 4 is a perspective view of a further modified version of the first embodiment of the present invention incorporating a sac locator groove at the distal end thereof and a tether lock at the proximal end thereof.
Figure 4A:
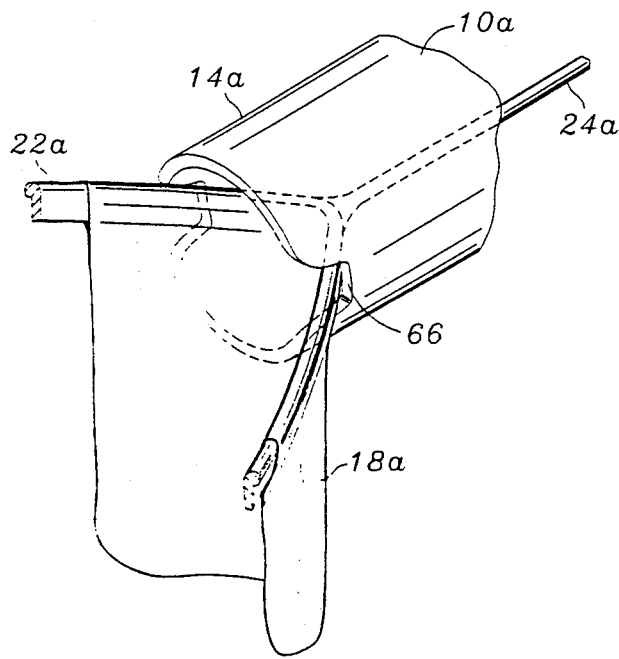
FIG. 4a is an enlarged perspective view of the distal end of the device shown in FIG. 4.

Referring now to FIGS. 3-3d and 4a, disclosed is a modified version of the first embodiment of the present invention. In the modified version, the deployment and retrieval system comprises an introducer 10a having a proximal end 12a and a distal end 14a. Interfaced to the introducer 10a is a sac 18a which is identically configured to the sac 18 previously disclosed. Attached to the sac 18a is a tether 24a which extends through the hollow lumen 16a of the introducer 10a such that when the sac 18a is deployed from the distal end 14a of the introducer 10a, a portion of the tether 24a will protrude from the proximal end 12a thereof, thereby enabling the rim member 22a and at least a portion of the sac 18a to be redrawn into the lumen 16a by grasping and pulling the protruding portion of the tether 24a in the proximal direction. As seen in FIG. 3a, the proximal end 12a of the introducer 10a includes a seal assembly 26a. As will be recognized, seal assembly 26a is substantially identical to the seal assembly 26 as previously described and includes a grip member 28a, a seal member 48a and a retainer member 54a having configurations identical to the grip member 28, seal member 48 and retainer member 54, respectively. As such, the seal assembly 26a differs from the seal assembly 26 only in that the proximal end 12a of the introducer 10a is formed having a flared portion 40a which is structurally equivalent to the flange member 40. By forming the flared portion 40a on the proximal end 12a of the introducer 10a, the necessity of having to separately adhere the flange member 40 to the introducer 10 as previously described is eliminated.

As best seen in FIGS. 3a and 3b, the flared portion 40a, like the flange member 40, includes a tapered portion 46a and an annular planar surface 44a. However, in the modified version of the first embodiment the annular surface 44a includes an annular bead 45 formed thereabout. Importantly, the seal assembly 26a is constructed in substantially the same manner as previously described with respect to seal assembly 26. Particularly, the grip member 28a is placed over the distal end 14a of the introducer 10a and moved along the length thereof until the annular inner surface 36a defined therein comes into abutting contact with the step 61a defined by the tapered portion 46a of the flared portion 40a. The seal member 48a is then placed upon the annular surface 44a of flared portion 40a and retained thereon by the threadable engagement of the male thread 58a of retainer member 54a to the female thread 34a of grip member 28a. In this respect, the seal member 48a is compressed between the annular surface 44a and an annular inner surface 62a defined within the bore 56a of retainer member 54a.

The insertion of the tether 24a through the seal assembly 26a occurs in substantially the same manner as previously described with respect to the tether 24 and seal assembly 26. In this respect, the tether 24a is inserted through an aperture 50a in the seal member 48a which is sized to establish a fluid-tight closure around the tether 24a while permitting the tether 24a to move back and forth therethrough. Additionally, the aperture 52a disposed in the seal member 48a is utilized to allow a plunger 64a to be inserted therethrough for purposes of moving the sac 18a from the compressed state to the deployed state. Additionally, when the plunger member 64a is not inserted therethrough, the aperture 52a biases to a "closed" configuration thereby preventing fluid flow through the lumen 16a.

Referring now to FIGS. 3d and 4a, in the modified version of the first embodiment, the distal end 14a of the introducer 10a is formed to include a locator notch 66 therein. The notch 66 is sized and configured to receive and engage a portion of the rim member 22a of the sac 18a in such a manner so as to prevent the sac 18a from undergoing at least rotational movement while the remainder of the sac 18a remains in an open configuration beyond the distal end 14a of the introducer 10a. As seen in FIG. 4a, the locator notch 66 is formed in opposed sides of the distal end 14a of the introducer 10a and is specifically sized to accommodate the rim member 22a of the sac 18a. To facilitate the engagement of the rim member 22a to the locator notch 66, the tether 24a is pulled in the proximal direction until the rim member 22a is received into the notch 66. Though, when such engagement occurs, the sac 18a is secured to the distal end 14a of the introducer 10a, the sac 18a remains open since the biasing action of the rim member 22a is not inhibited by the notch 66. As seen in FIG. 3d, the inner diameter of the distal end 14a of the introducer 10a is further provided with a chamfered portion 68. Importantly, the chamfered portion 68 is utilized to aid in the reinsertion of the sac 18a into the lumen 16a of the introducer 10a when the sac 18a is partially retracted during the utilization of the system.

Referring now to FIGS. 3 and 3c, as previously specified, the distal end 14a of the introducer 10a includes a chamfered portion 68 formed on the inner diameter thereof to aid in partially retracting the sac 18a into the lumen 16a. In addition to being utilized for this purpose, the chamfered portion 68 is also used to assist in disposing the sac 18a into its compressed state within the lumen 16a during the preparation of the present system for use in a surgical procedure. To provide further assistance in initially disposing the sac 18a into its compressed state, the modified version of the first embodiments further includes a guide member 70 which is selectively attachable to the distal end 14a of the introducer 10a. As best seen in FIG. 3c, guide member 70 includes a bore 72 extending axially therethrough which defines a step 74 therewithin for limiting the distance guide member 70 slides along the outer surface of the introducer 10a. The end of bore 72 opposite that interfaced to the distal end 14a of introducer 10a includes a chamfered portion 76 to facilitate entry of the sac 18a thereinto. Thus, when initially preparing the device for use in a surgical procedure, the guide member 70 is placed upon the distal end 14a of the introducer 10a in the aforementioned manner. The tether 24a of the sac 18a is then extended through the guide member 70, lumen 16a and seal assembly 26a. When the tether 24a is pulled in the proximal direction, the chamfered portion 76 of the guide member 70 as well as the chamfered portion 68 formed in the distal end 14a of the introducer 10a provides substantial assistance in disposing the sac 18a into its compressed state within the lumen 16a. After the sac 18a has been disposed in its compressed state, the guide member 70 is removed from the distal end 14a of the introducer 10a.

Figure 4B:
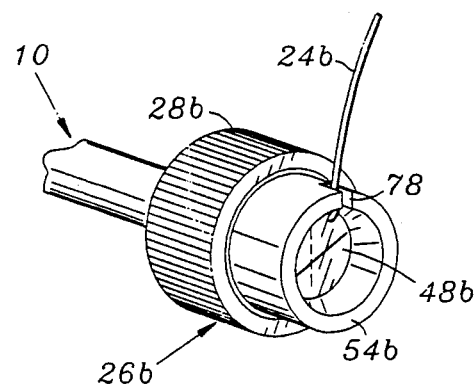
FIG. 4b is an enlarged perspective view of the proximal end of the device shown in FIG. 3.

Referring now to FIGS. 4 and 4b, illustrated is a further modified version of the first embodiment of the present invention which is substantially identical to the modified version of the first embodiment previously described. The further modified version of the first embodiment comprises an introducer 10b having a proximal end 12b and a distal end 14b. Interfaced to the introducer 10b is a containment sac 18b having a tether 24b connected thereto which extends through the introducer 10b. The proximal end 12b of the introducer 10b includes a seal assembly 26b which is substantially identical to the seal assembly 26a described with respect to the modified version of the first embodiment. In this respect, seal assembly 26b differs from seal assembly 26a only in the structure of the retainer member 54b thereof. Particularly, the retainer member 54b includes a tether receiving slot 78 formed therein which is configured to releasably grip and hold the tether 24b in a fixed position relative to the introducer 10b. The slot 78 is preferably sized relative to the tether 24b such that the tether 24b may be press fit thereinto and be frictionally engaged thereby to hold the tether 24b in a fixed position. Though retainer member 54b is formed to include slot 78, it will be recognized that other than for the inclusion of slot 78, the retainer member 54b is identically configured to the retainer members 54a. As such, the retainer member 54b, seal member 48b, grip member 28b and flared end of the introducer 10b are interconnected in the same manner as previously discussed with respect to seal assembly 26a in constructing seal assembly 26b.

Referring now to FIGS. 5-5d, illustrated is a device for deploying and retrieving a flexible tissue containment sac within a body cavity constructed in accordance with a second embodiment of the present invention. The device constructed in accordance with the second embodiment generally comprises a tubular introducer 110 having a proximal end 112, a distal end 114 and a hollow lumen 116 extending longitudinally therethrough. Slidably received into the lumen 116 of the introducer 110 is a rigid shaft member 126 having a proximal end 128 and a distal end 130. Positioned on the distal end 130 of the shaft 126 is a containment sac 118. The containment sac 118 is rigidly secured to the distal end 130 of the shaft 126 via the attachment of the rim member 122 thereto.

Disposed on the proximal end 128 of the shaft 126 is a handle member 132 having a generally cylindrical configuration. In the second embodiment, the shaft 126 is slidably movable within the lumen 116 of the introducer 110 by selectively moving the handle member 132 in a proximal or distal direction. Particularly, the shaft 126 is movable between a first position wherein the sac 118 is withdrawn into the lumen 116 of the introducer 110 (as shown in FIG. 5d) and a second position wherein the sac 118 is deployed beyond the distal end 114 of the introducer 110 (as shown in FIG. 5a). The handle member 132 is preferably formed having an enlarged configuration so as to be larger, i.e. have a larger outer diameter dimension, than the lumen 116 of the introducer 110 such that the shaft 126 can only be inserted into the introducer 110 to a point where the handle member 132 abuts against the proximal end 112 of the introducer 110.

Referring now to FIG. 5b, the proximal end 112 of the introducer 110 includes an enlarged cylindrical sleeve 134 positioned thereon. The cylindrical sleeve 134 is formed having an outer diameter dimension approximately equal to the outer diameter dimension of the cylindrical handle member 132. The sleeve 134 is preferably interfaced to the outer surface of the introducer 110 via an adhesive, though other bonding processes may be utilized as an alternative. Disposed in the proximal end of the sleeve 134 is a seal member 136 having a bore extending axially therethrough which is sized and configured to receive the shaft 126 and establish a fluid-tight closure thereabout while permitting the shaft 126 to move back and forth therethrough. As will be recognized, the insertion of the shaft 126 into the introducer 110 will be limited by the abutment of the handle member 132 against the seal member 136.

Formed in the distal end 114 of the introducer 110 is a notch 138 which is utilized for the same purposes as the notch 66 described with respect to the modified version of the first embodiment. In this regard, the notch 138 is specifically sized and configured to receive the rim member 122 of the containment sac 118 so as to substantially prevent rotation thereof. The shaft 126, in addition to being axially movable within the lumen 116 of introducer 110, is also rotatable therewithin as designated by the arrow shown in FIG. 5. As such, by rotating the handle member 132 and thus the shaft 126, the rim member 122 may be easily positioned within the notch 138. After having tissues, organs, etc. inserted thereinto, the sac 118 is partially retracted into the lumen 116 (as shown in FIG. 5c) by pulling the handle member 32 in the proximal direction. As will be recognized, in the second embodiment, the distance separating the sac 118 from the distal end 114 of the introducer 110 is limited to the length of the shaft 126 that extends beyond the distal end 114 when the handle member 132 is abutted against the seal member 136.

Referring now to FIGS. 8a and 8b, disclosed is an alternative method of connecting the rim member 122 of the sac 118 to the distal end 130 of the shaft 126 to facilitate the opening and closing of the sac 118. As previously specified, in the second embodiment shown in FIGS. 5-5d, the rim member 122 is rigidly secured to the distal end 130 of the shaft 126. Though the sac 118 is biased open by the rim member 122 when such is deployed from the distal end 114 of introducer 110, the rim member 122 is not adapted to close the sac 118 when deployed. Rather, the sac 118 is closed only when the rim member 122 and portions of the sac 118 are retracted into the lumen 116 of the introducer 110 by the shaft 126. Additionally, though the rim member 122 biases the sac 118 to an open position when deployed, often times the aperture 120 defined by the rim member 122 is not large enough to accommodate the tissues that are to be inserted into the sac 118. To alleviate this deficiency, the rim member 122 shown in FIGS. 8a and 8b is formed from a single, elongate element which is sized so as to extend completely through the interior of the shaft 126. In this respect, rim member 122 defines a first portion 140 and a second portion 142 which each extend through shaft 126. First portion 140 is secured to the distal end 130 of shaft 126 by an adhesive layer 144 or other suitable connection method. Though first portion 140 is rigidly secured to the distal end 130 of the shaft 126, the second portion 142 is free to slide axially within the interior of the shaft 126. As such, by pulling the second portion 142 in the proximal direction (designated by the arrow in FIG. 8a), the rim member 122 is collapsed thereby closing the aperture 120 of the containment sac 118. Conversely, by sliding the second portion 142 in the distal direction (designated by the arrow in FIG. 8b), the rim member 122 is caused to fully open the aperture 120 of the containment sac 118. As will be recognized, by fabricating the rim member 122 in the aforementioned manner, the obtainable size of the aperture 120 of the containment sac 118 is not entirely dependent upon the resiliency of the materials used for the rim member 122. Importantly, in interfacing the rim member 122 to the sac 118 in the manner shown in FIGS. 8a and 8b, the rim member 122 will not be attached to the sac 118 via a heat fusion process in the manner previously described since the rim member 122 must necessarily be able to slide freely relative the sac 118. Though the sac 118 is not fused to the rim member 122, the sac is rigidly attached to the distal end 130 of shaft 126 via an adhesive or a heat fusion process so as to maintain the positioning of the sac 118 while the rim member 122 is being adjusted relative thereto.

Referring now to FIGS. 6 and 7, illustrated is a modified version of the second embodiment of the present invention. The modified version of the second embodiment generally comprises an introducer 110a having a proximal end 112a and a distal end 114a. The introducer 110a is identically configured to the introducer 110 and includes a notch 138a formed in the distal end 114a thereof. Slidably received into the lumen 116a of the introducer 110a is a rigid shaft 126a having a proximal end 128a and a distal end 130a. Interfaced to the shaft 126a is a containment sac 118a having a rim member 122a defining an open aperture 120a which provides access to the interior of sac 118a. Disposed on the proximal end 128a of shaft 126a is an enlarged handle member 132a which, like handle member 132, is larger than the lumen 116a of the introducer 110a such that the shaft 126a can only be inserted into the introducer 110a to a point where the handle member 132a abuts against the proximal end 112a of the introducer 110a. The handle member 132a is identically configured to the handle member 132 except that handle member 132a includes a slot 146 disposed therein for reasons which will be discussed in greater detail below. The proximal end 112a of the introducer 110a includes a sleeve 134a disposed thereon which is identically configured to the sleeve 134 previously described. Additionally, disposed in the proximal end of the sleeve 134a is a seal member 136a which establishes a fluid-tight closure around the shaft 126a while permitting the shaft 126a to move back and forth therethrough.

As seen in FIG. 7, the proximal end 130a of the shaft 126a is formed to include a secondary notch 148 which, like notch 138a, is used to receive and prevent the rotation of the rim member 122a. In the modified version of the second embodiment, the rim member 122a is rigidly secured to a lock member 150 having a tapered configuration with a maximum outer diameter dimension exceeding the inner diameter dimension of the shaft 126a. Attached to the lock member 150 is a tether 124. In interfacing the sac 118a to the shaft 126a, the tether 124 is extended through the shaft 126 and into the handle member 132a. The tether receiving slot 146 formed in the handle member 132a is sized relative to the tether 124 such that the tether 124 may be frictionally retained within the slot 146 to hold the tether 124 in a fixed position relative the shaft 126a. In the modified version of the second embodiment shown in FIGS. 6 and 7, the containment sac 118a may be removed from its engagement with the distal end 130a of the shaft 126a thereby allowing the sac 118a to be selectively positioned within the abdominal cavity of the patient. When the sac 118a is initially moved from its compressed state within the lumen 116a of the introducer 110a to the deployed state within the abdominal cavity, the lock member 150 is frictionally retained within the distal end 130a of the shaft 126a due to its tapered configuration. After the sac 118a has been deployed, forceps or other surgical instruments may be utilized to grasp the rim member 122a and pull the sac 118a in a distal direction, thereby releasing the lock member 150 from its engagement with the shaft 126a. Importantly, as the sac 118a is being pulled, the tether 124 is not disposed within the slot 146. However, when the sac 118a has been properly positioned in the abdominal cavity, the sac 118a is prevented from further movement by securing the positioning of the tether 124 via the receipt thereof into the slot 146. After the tissues, organs, etc. have been introduced into the sac 118a via the aperture 120a, the tether 124 is disengaged from the slot 146 and pulled proximally thereby drawing the lock member 150 back into the distal end 130a of the shaft 126a. The tether 124 is pulled until the lock member 150 re-engages the shaft 126a. After such engagement occurs, the handle member 132a is pulled proximally to retract the rim member 122a and a portion of the sac 118a into the lumen 116a of the introducer 110a.

Referring now to FIGS. 9a-11b, disclosed are alternative methods of fabricating the containment sac of the present invention to facilitate the opening thereof when such is deployed into the abdominal cavity of the patient. It will be recognized that though the following descriptions are directed to the sac 18a used in the embodiment shown in FIG. 3, the disclosed sacs may also be utilized as alternatives to the sacs 18, 18b, 118 and 118a previously described.

Figure 9A:
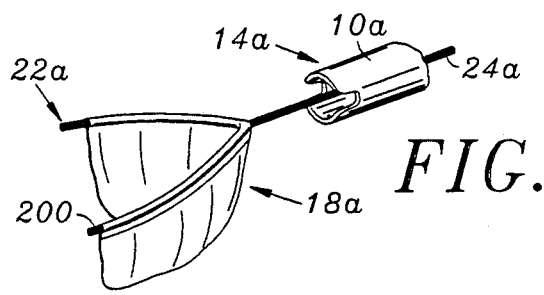
FIG. 9a is an illustration of the distal portion of a device in accordance with the first embodiment of the present invention incorporating a spring metal sac opening feature formed of multiple loops of spring metal wire.
Figure 9B:
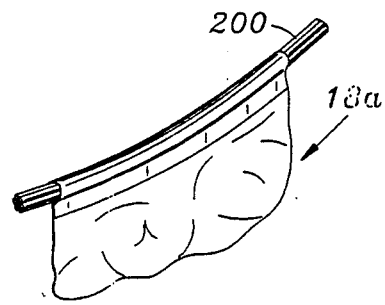
Figure 10:
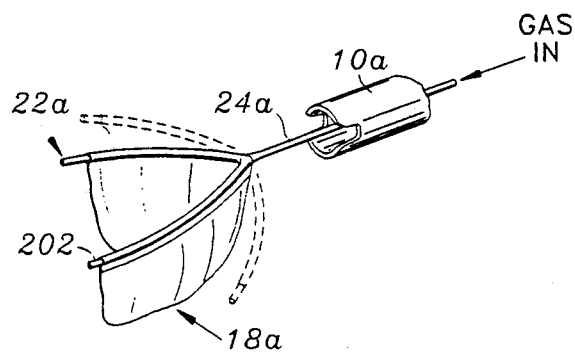
FIG. 10 is a perspective view of the distal portion of a device in accordance with the first embodiment of the present invention incorporating an inflatable sac opening apparatus.
Figure 11:
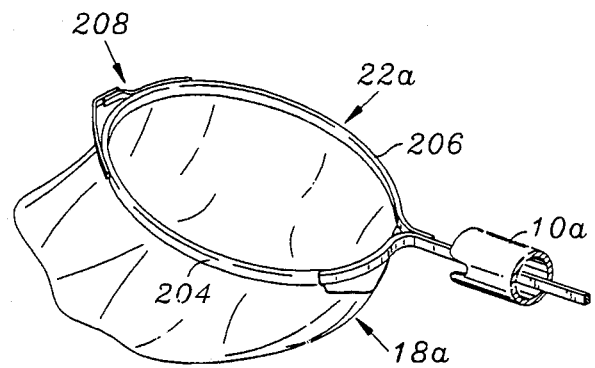
FIG. 11 is a perspective view of the distal portion of a device in accordance with the first embodiment of the present invention incorporating a spring-biased sac opening apparatus.
Figure 11B:
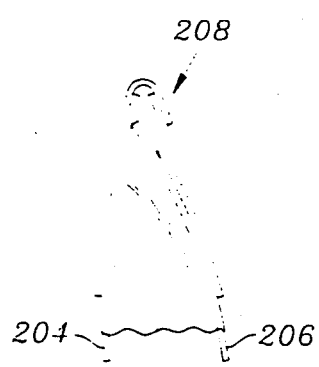
FIG. 11b is an elevational view showing the spring biased opening apparatus of the device of FIG. 11 in a "collapsed" configuration.
Figure 11A:
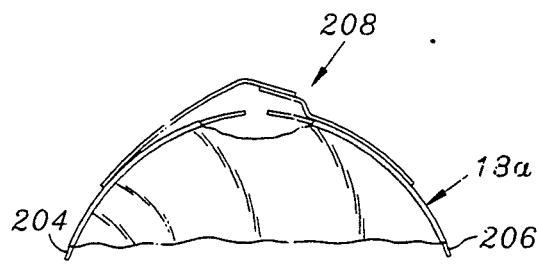
FIG. 11a is an elevational view showing the spring biased opening apparatus of the device of FIG. 11 in an "open" configuration.

As seen in FIGS. 9a and 9b, the rim member 22a may comprise spring metal wire which is formed into multiple loops 200 so as to supply sufficient resiliency to bias the sac 18a to an open position. In this embodiment, the tether 24a also comprises spring metal wire and is directly connected to the wire loops 200. As seen in FIG. 10, the rim member 22a may comprise a hollow inflatable member 202 which is in fluid communication with a hollow tether 24a. In this respect, when gas is passed through the hollow tether 24a as shown in FIG. 10, the member 202 is inflated thus fully opening the containment sac 18a. To close the containment sac 18a in the embodiment shown in FIG. 10, the gas is withdrawn from the inflatable member 202 thereby collapsing the member 202 and causing the rim member 22a to close the containment sac 18a. As seen in FIGS. 11-11b, the rim member 22a may further comprise first 204 and second 206 rim member portions fabricated from plastic wherein the first rim portion 204 is connected to the second rim member portion 206 via a spring 208. In operation, the spring 208 is adapted to urge the first and second rim member portions 204, 206 in divergent directions to thereby bias the sac 18a to an open configuration. In the present invention, each of the aforementioned containment sacs may include a quantity of lubricant disposed thereon to facilitate passage of the sac into and out of the lumen of the introducer. The lubricant and/or surface modified layer is preferably selected from the group of materials consisting essentially of glycerin, silicone, polyacrylamide, polyvinylpyrrolidone, and possible combinations thereof. It will be appreciated that these materials may be spread on the outer surface of the sac or may be impregnated in or formed as a separate surface layer disposed on the appropriate portion(s) of the sac. Additionally, each of the sacs are preferably formed of transparent material and comprise a single walled sac which is approximately 2.5 inches in diameter and approximately 5 inches in length. Importantly, by forming the sacs from transparent material, the surgeon is able to observe the placement of tissues, organs, etc. into the sac.

In any embodiment of the invention, the flexible containment sac may be formed of any suitable material or combination of materials capable of performing the function of the containment sac. The materials of which the containment sac may be formed include, but are not limited to, materials selected from the group consisting essentially of polyethylene, nylon, vinyl, styrene-butadiene copolymers, nylon-olefin laminate and the possible combinations thereof.

In the present invention, the introducers 10, 10a, 10b, 110 and 110a are each sized to be insertable through a standard laparoscopy portal. In this respect, the introducers are fabricated having a length of approximately 3-20 inches, internal diameters of 0.20-0.60 inches and outer diameters of approximately 0.230-0.630 inches. Additionally, the introducers are preferably formed of material(s) selected from the group consisting essentially of polytetrafluoroethylene, polycarbonate, PVC and combinations thereof.

Having thus described the components comprising various embodiments of the present invention and variations thereof, examples of methods of utilizing the invention will now be explained.

Examples of Methods for Utilizing the Present Invention

Either of the above-described embodiments of the invention may be used to contain and facilitate removal of various types of tissue or material from various areas or cavities of the body.

In either embodiment of the invention, the flexible containment sac 18, 118 is initially withdrawn into the lumen of the introducer 10, 110. The introducer 10, 110 is then inserted, distal end first, through a portal which has been placed through the small incision or opening into a body cavity. The containment sac 18, 118 is then expelled out of the distal end of the introducer by advancement of the plunger 64 or shaft member 126. When the containment sac 18, 118 has been deployed out of the distal end of the introducer 10, 110, the aperture 20, 120 of the containment sac 18, 118 is opened and the desired organ, tissue or material is inserted into the sac 18, 118. Such insertion of the desired organ, tissue or material into the sac may be carried out through the use of intracorporeally inserted instruments, under endoscopic visualization.

After the desired organ, tissue or material has been inserted into the containment sac 18, 118, such containment sac is partially withdrawn into the lumen 16, 116 of the introducer 10, 110 such that the aperture or opening 20, 120 of the sac 18, 118 is completely or substantially within the lumen 16, 116 of the introducer 10, 110 while the filled body of the sac 18, 118 remains outboard of the distal end of the introducer 10, 110. The introducer 10, 110 is then extracted from the opening or incision together with the laparoscopic portal, thereby withdrawing along with it the aperture 20, 120 and upper portion of the sac 18, 118. Thereafter, the device and portal may be separated from the sac 18, 118, leaving the opening or aperture 20, 120 of the sac 18, 118 in an exteriorized position, while the filled body of the sac 18, 118 remains within the body cavity. Various instruments for debulking, crushing, liquidizing, grinding, mulching or otherwise treating the organ, tissue or material within the sac 18, 118 may then be inserted through the exteriorized aperture 20, 120 and into the body of the sac. After any desired debulking, crushing, liquidization, grinding, mulching or other treatment of the sac contents has been completed, the contents of the sac may be fully or partially aspirated or removed therefrom, thereby rendering the body of the sac 18, 118 sufficiently collapsible or compressible to be pulled through the relatively small body opening or incision.

Currently, one specific operative procedure wherein the device of the present invention may be utilized is that known as the "laparoscopic cholecystectomy". FIGS. 12 and 13a-g illustrate a preferred manner in which the modified second embodiment of the invention shown in FIG. 6 of the drawings may be utilized in the performance of a laparoscopic cholecystectomy.

Figure 12:
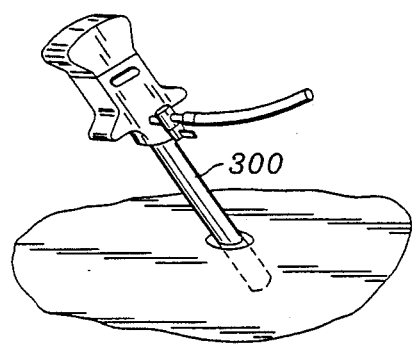
FIG. 12 is a schematic illustration of a standard laparoscopy portal device inserted into the abdomen of a human being.

As shown in FIG. 12, a standard laparoscopy portal 300 is inserted into the abdominal cavity through a small (e.g. 1 cm) periumbilical incision. Carbon dioxide is passed into the abdominal cavity to create a distended pneumoperitoneum. One or more secondary portals or accessory portals are inserted at other sites for passage of instruments and/or laparoscopes into the abdominal cavity.

During the hereinafter described removal procedure, a laparoscope remains inserted through a secondary portal or accessory portal so as to permit visualization of the containment sac 118a during intra-abdominal deployment and manipulation thereof.

Prior to utilization of the device, the flexible sac 118a is fully withdrawn into the lumen 116a of the introducer 110a by grasping handle member 132a and pulling in the proximal direction.

Figure 13:
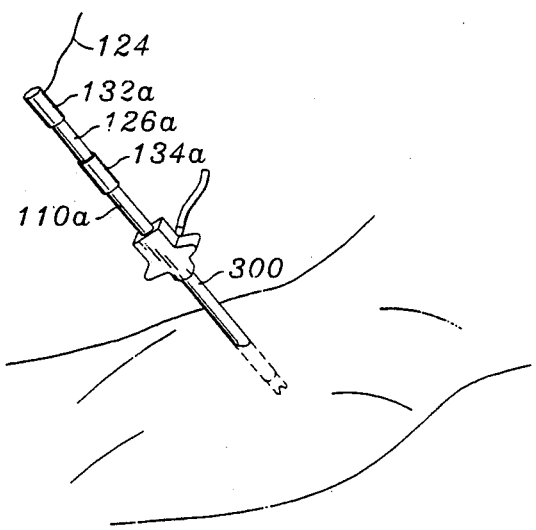
FIG. 13 is a schematic diagram showing a device in accordance with the second embodiment of the invention inserted into the abdomen through a standard laparoscopy portal.

With the flexible containment sac 118a fully disposed within the lumen 116a of the introducer 110a, the introducer 110a is inserted through portal 300 to a point where the distal end 114a of the introducer 110a is slightly beyond the tip of the portal 300 (FIG. 13).

Figure 13A:
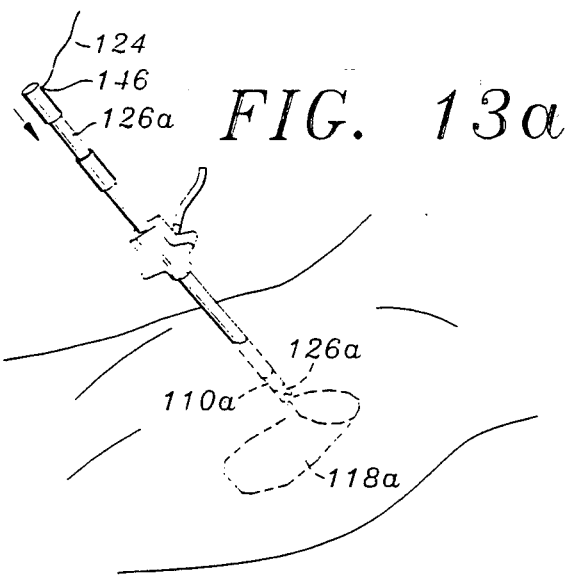
FIG. 13a is a schematic illustration showing the initial deployment of a flexible containment sac out of the distal end of the introducer of the device of the second embodiment, of the present invention.
Figure 13C:
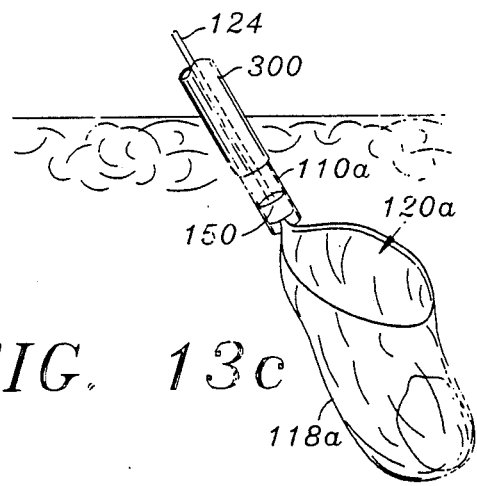
FIG. 13c is a schematic illustration showing the manner in which the flexible containment sac is reattached to the shaft portion of a device in accordance with the second embodiment of the present invention.
Figure 13B:
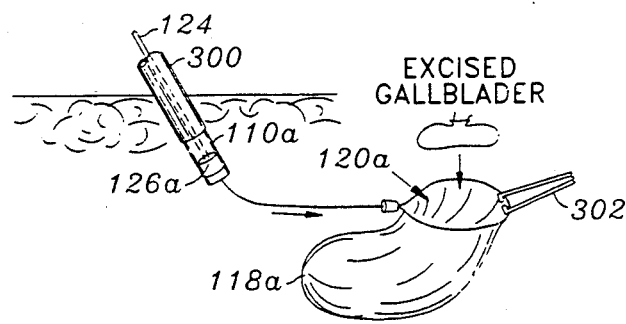
FIG. 13b is a schematic diagram illustrating detachment and movement of the flexible containment sac from the distal end of the introducer of the device of the second embodiment of the present invention.

Thereafter, the shaft 126a is advanced in a distal direction to cause the containment sac 118a to be deployed out of the distal end 114a of the introducer 110a. A small portion of shaft 126a may also emerge from the distal end of introducer 110a as shown (FIG. 13a).

Upon deployment of the flexible containment sac 118a out of the distal end 114a of introducer 110a, the aperture 120a of the containment sac 118a will assume an open position as a result of the biased rim member 122a disposed within the rim of the aperture 20a. The tether 124 is released from tether lock 146 and a pair of blunt forceps 302 are utilized to grasp the rim member 122a of containment sac 118a and to tug or extract the lock member 150 from within the distal end 130a of shaft 126a. The containment sac 118a may then be moved to a position adjacent the in situ gallbladder. The gallbladder is then excised and inserted, through aperture 120a into the containment sac 118a.

After the gallbladder has been placed within sac 118a, the sac is returned to a position adjacent the distal end of the shaft 126a and tether 124a is withdrawn in a proximal direction to cause the lock member 150 to once again seat within shaft 126a. After the lock member 150 has seated within shaft 126a, the tether 124 is drawn and locked within tether lock 146.

Figure 13D:
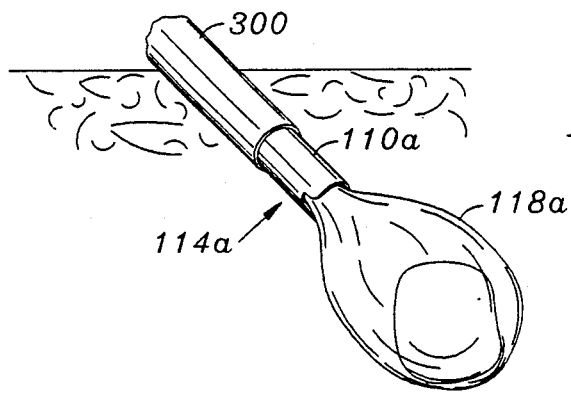
FIG. 13d is a schematic diagram illustrating the manner in which the filled containment sac is partially withdrawn into the introducer portion of the device in accordance with the second embodiment of the present invention.

Thereafter, the handle member 132a is grasped and shaft 126a is withdrawn in a proximal direction to a point where the aperture 120a, rim member 122a and upper portion of sac 118a have been fully retracted into the lumen 116a of the introducer 110a. The gallbladder-filled body of the sac 118a remains beyond the distal end 114a of the introducer 110a (FIG. 13d). Such withdrawal of the aperture 120a, rim member 122a and upper portion of sac 118a into the lumen 116a of the introducer 110a effects sealing and closure of the sac 118a to minimize the likelihood of leakage from the interior of sac 118a.

Figure 13F:
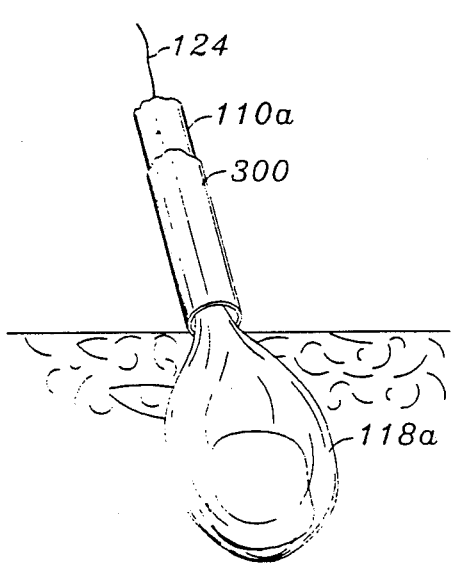
FIG. 13f is a schematic diagram illustrating the filled containment sac following exteriorization of a portion thereof.
Figure 13E:
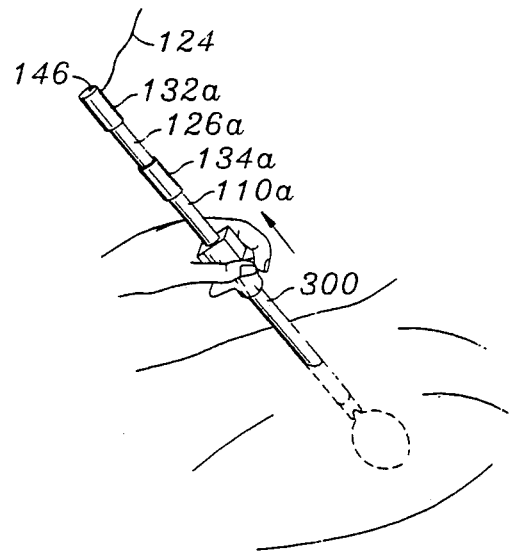
FIG. 13e is a schematic diagram illustrating the manner in which the laparoscopy portal and the device of the present invention are concomitantly withdrawn out of the abdomen causing exteriorization of a portion of the filled containment sac.
Figure 13G:
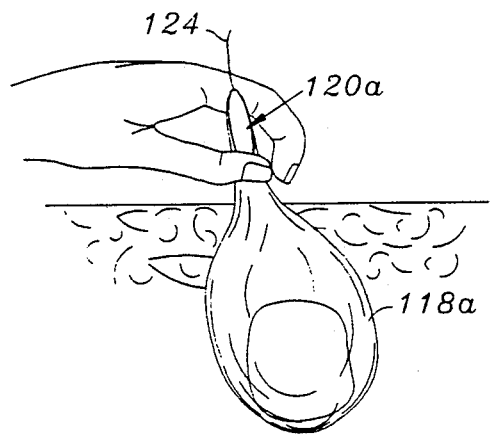
FIG. 13g illustrates the partially exteriorized filled containment sac after removal of the device of the present invention and cutting or severance of the tether extending from the flexible containment sac.

Thereafter, the tether 124 is removed from tether lock 146 and the entire device, along with the portal 300 are extracted from the periumbilical incision. Only the filled portion of sac 118a remains within the abdomen. The upper portion of the sac 118a including its aperture 120a are fully exteriorized (FIG. 13f).

Thereafter, the entire device, along with the portal 300, may be fully withdrawn over the proximal end of tether 124 and discarded, leaving only the sac 118a and tether 124 connected to the body.

At this point, the surgeon may opt to apply pulling force to the sac 118a to attempt to remove the gallbladder-filled sac 118a through the periumbilical incision. If the gallbladder-filled portion of the sac 118a is too large to be pulled through the incision, a debulking instrument such as that available under the trademark LAPAROLITH ™ (Baxter Healthcare Corporation, Technology & Ventures Division, Irvine, Calif.) may be inserted through aperture 120a into the sac 118a for the purpose of debulking and removing the gallbladder as well as any stones or other contents thereof.

After the gallbladder and its contents have been debulked and/or removed from sac 118a, the body of the sac 118a may be easily pulled out of the periumbilical incision and the incision may be closed using standard closure techniques.

Although the above-described procedure has been stated in terms of a standard excisional cholecystectomy, it will be appreciated that the same technique may be employed to carry out a lithotripsy procedure wherein, rather than excising and removing the entire gallbladder, the gallbladder is opened and the stones are removed from the interior of the gallbladder and placed within the containment sac 118a. The opening in the gallbladder is then closed by way of clips or sutures and the remainder of the procedure is carried out as stated above for the excisional cholecystectomy.

The above-described methodology is but one example of an operative procedure that may be carried out using a device of the present invention. It will be appreciated that other embodiments of the invention may be employed in other procedures, all of which are within the intended scope of the present application.

The present invention has been described herein with reference to presently preferred embodiments of the device and with reference to specific examples of methods of using the device. The foregoing description of the preferred embodiments and examples of the method are not intended to limit the invention in any way. In fact, by applying current or future knowledge, those skilled in the art will recognize numerous modifications, substitutions, deletions or alterations which may be made to the above-described preferred embodiments and examples without departing from the spirit and scope of the present invention. It is intended that all such modifications, substitutions, deletions or alterations be included within the scope of the following claims and the equivalents thereof.

What is claimed is:

1. A system for deploying and retrieving a flexible non-porous tissue containment sac within a body cavity, said system comprising:
   a tubular introducer having a distal end, a proximal end and a hollow lumen extending longitudinally therethrough;
   a rigid shaft member having a distal end and a proximal end, the distal end of said rigid shaft member being positioned with the lumen of said introducer;
   a flexible non-porous containment sac positioned on the distal end of said shaft, said sac having an aperture formed therein and a rim member associated with said aperture to cause said aperture to assume an open configuration;
   said rim member having first and second rim member portions, said first rim member portion being connected to said second rim member portion by way of a spring such that said spring will urge said first and second rim member portions in divergent directions to thereby bias said aperture in an open configuration;
   said shaft member being alternately moveable within the lumen of said introducer between:
      a first initial position wherein said containment sac is fully withdrawn into and contained within the lumen of said introducer;
      a second position wherein said containment sac is fully deployed out of and beyond the distal end of said introducer; and
      a third position wherein the aperture of said containment sac is retracted into the introducer, thereby substantially closing said aperture and preventing leakage from said containment sac.

2. The system of claim 1 wherein an enlarged handle is formed on the proximal end of said shaft, said enlarged handle being larger than the lumen of said introducer such that said shaft can only be advanced distally through said introducer to a point where said handle abuts against the proximal end of said introducer.

3. The system of claim 1 wherein said containment sac may be detached from and reattached to the distal end of said shaft and wherein said system further comprises:
   a hollow lumen extending longitudinally through said shaft;
   a tether connected to said containment sac and extending through the lumen of said shaft such that a proximal portion of said tether extends out of the proximal end of said shaft;
   said tether being distally extendable and proximally retractable back and forth through said shaft such that said containment sac may, while remaining connected to said tether, may be;
      (i) detached from said shaft and transferred to a remote location beyond the distal end of said shaft and
      (ii) subsequently, returned to and reattached to the distal end of said shaft by proximal retraction of said tether through said shaft.

4. The system of claim 3 further comprising:
   a tether lock apparatus positioned on said shaft, said tether lock apparatus being configured to releasably grip and hold said tether in a fixed position relative to said shaft.

5. The system of claim 4 wherein said tether lock apparatus comprises a tether receiving slot formed in the proximal end of said shaft and sized relative to said tether such that said tether may be press fit into said slot and frictionally engaged thereby to hold said tether in a fixed position relative to said shaft.

6. The system of claim 1 further comprising a quantity of lubricant disposed on said sac to facilitate passage of said sac into and out of the lumen of said introducer.

7. The system of claim 6 wherein said lubricant is selected from the group consisting essentially of:
   glycerin; and
   silicone.

8. The system of claim 1 further comprising a shaft seal disposed at least partially within the lumen of said introducer to form a fluid tight seal within the introducer lumen around said elongate shaft.

9. The system of claim 1 wherein said introducer is sized to be insertable through a standard laparoscopy portal.

10. The system of claim 1 wherein said introducer is approximately 3–20 inches in length.

11. The system of claim 1 wherein said introducer has in internal diameter of 0.20–0.60 inches in length.

12. The system of claim 1 wherein said introducer has an outer diameter of approximately 0.230–0.630 inches in length.

13. The system of claim 1 wherein said sac is transparent.

14. The system of claim 1 wherein said sac comprises a single walled sac, with reinforcements at stress points.

15. The system of claim 1 wherein said sac comprises a single walled transparent sac.

16. The system of claim 1 wherein said sac is approximately 2.5 inches in diameter and approximately 5 inches in length.

17. The system of claim 1 wherein said sac is formed of material(s) selected from the group consisting essentially of:
polyethylene;
nylon;
vinyl;
styrene-butadiene copolymers;
nylon-olefin laminate; and
combinations thereof.

18. The system of claim 1 wherein said introducer is formed of material(s) selected from the group consisting essentially of:
(a) polytetrafluoroethylene;
(b) polycarbonate; and
(c) polyvinyl chloride.

19. The system of claim 1 wherein the rim member of said sac is attached to the distal end of said shaft.

20. A system for deploying and retrieving a flexible non-porous tissue containment sac within a body cavity, said system comprising:
a tubular introducer having a distal end, a proximal end and a hollow lumen extending longitudinally therethrough;
a rigid shaft member having a distal end and a proximal end, the distal end of said rigid shaft member being positioned with the lumen of said introducer;
a flexible non-porous containment sac positioned on the distal end of said shaft, said sac having an aperture formed therein and a rim member disposed about said aperture to cause said aperture to assume an open configuration;
said rim member comprising a strip fused to said sac;
said shaft member being alternately moveable within the lumen of said introducer between:
a first initial position wherein said containment sac is fully withdrawn into and contained within the lumen of said introducer;
a second position wherein said containment sac is fully deployed out of and beyond the distal end of said introducer; and
a third position wherein the aperture of said containment sac is retracted into said introducer, thereby substantially closing said aperture and preventing leakage from said containment sac.

21. The system of claim 20 wherein said rim member comprises:
a loop of pliable material and a elongate extension attached to one end of said loop and extending longitudinally through said shaft, said elongate extension being slidably movable in proximal and distal directions within said shaft such that:
(a) advancement of said elongate extension in the distal direction will cause enlargement of said rim member loop; and
(b) retraction of said elongate extension in the proximal direction will cause contraction of said rim member loop.

22. The system of claim 20 wherein an enlarged handle is formed on the proximal end of said shaft, said enlarged handle being larger than the lumen of said introducer such that said shaft can only be advanced distally through said introducer to a point where said handle abuts against the proximal end of said introducer.

23. The system of claim 22 wherein said introducer is sized to be insertable through a standard laparoscopy portal.

24. The system of claim 20 wherein said rim member comprises a plastic strip.

25. The system of claim 20 wherein said rim member strip comprises spring metal wire.

26. The system of claim 20 wherein said rim member strip comprises multiple loops of spring metal wire.

27. The system of claim 20 wherein said rim member strip comprises a superelastic metal alloy.

28. The system of claim 27 wherein said superelastic metal alloy comprises nickel-titanium.

29. The system of claim 20 further comprising a quantity of lubricant disposed on said sac to facilitate passage of said sac into and out of the lumen of said introducer.

30. The system of claim 29 wherein said lubricant is selected from the group consisting essentially of:
glycerin; and
silicone.

31. The system of claim 20 further comprising a shaft seal forming a fluid tight seal within the introducer lumen around said elongate shaft.

32. The system of claim 20 wherein said introducer is approximately 3–20 inches in length.

33. The system of claim 20 wherein said introducer has in internal diameter of 0.20–0.60 inches in length.

34. The system of claim 20 wherein said introducer has an outer diameter of approximately 0.230–0.630 inches in length.

35. The system of claim 20 wherein said sac is transparent.

36. The system of claim 20 wherein said sac comprises a single walled sac, with reinforcements at stress points.

37. The system of claim 20 wherein said sac comprises a single walled transparent sac.

38. The system of claim 20 wherein said sac is approximately 2.5 inches in diameter and approximately 5 inches in length.

39. The system of claim 20 wherein said sac is formed of:
polyethylene;
nylon;
vinyl;
styrene-butadiene copolymers;
nylon-olefin laminate; and
combinations thereof.

40. The system of claim 20 wherein said introducer is formed of material(s) selected from the group consisting essentially of:
(a) polytetrafluoroethylene;
(b) polycarbonate; and
(c) polyvinyl chloride.

41. The system of claim 20 wherein said rim member strip is directly attached to the distal end of said shaft.

* * * * *